United States Patent
Paidi et al.

(10) Patent No.: US 6,437,130 B1
(45) Date of Patent: Aug. 20, 2002

(54) PYRIDINE DERIVATIVE AND ITS COMPLEX

(75) Inventors: Reddy Yella Paidi, Secunderabad (IN); Masayuki Ito, Aichi-ken (JP)

(73) Assignee: Aisin Seiki Kabushiki Kaisha, Kariya (JP)

( * ) Notice: Subject to any disclaimer, the term of this patent is extended or adjusted under 35 U.S.C. 154(b) by 0 days.

(21) Appl. No.: 10/024,378

(22) Filed: Dec. 21, 2001

(30) Foreign Application Priority Data

Dec. 21, 2000 (JP) ........................................ 2000-389181

(51) Int. Cl.[7] .......................... H01L 31/00; C07F 15/00; C07D 213/22
(52) U.S. Cl. ............................ 546/8; 546/257; 136/252; 136/256; 136/263
(58) Field of Search ...................... 546/8, 257; 136/252, 136/256, 263

(56) References Cited

PUBLICATIONS

Sprintschnik et al, "Preparation and Photochemical Reactivity of Surfactant Ruthenium (II) Complexes In Monolayer Assemblies and at Water–Solid Interfaces[1,2]", Journal of the American Chemical Society/99:15/Jul. 20, 1977.

Eggleston et al, "Structural Variations Induced by Changes in Oxidation State and Their Role in Electron Transfer. Crystal and Molecular Structures of cis–[Ru(bpy)$_2$Cl$_2$] –3.5H$_2$O and cis–[Ru(bpy)$_2$Cl$_2$]Cl–2H$_2$O" Inorganic Chemistry, vol. 24, No. 26, 1985.

Primary Examiner—Bernard Dentz
(74) Attorney, Agent, or Firm—Oblon, Spivak, McClelland, Maier & Neustadt, P.C.

(57) ABSTRACT

A pyridine derivative exhibiting a photoelectric conversion is represented by formula

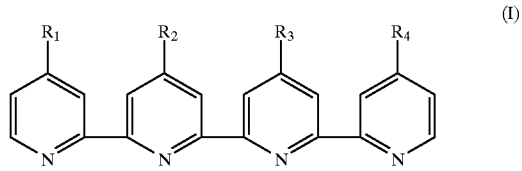

(I)

wherein each of $R_1$, $R_2$, $R_3$, $R_4$ is independently —OR', —COOR', —CONR', —CHO, —CH$_2$OR', —CN, an alkyl group whose carbon number ranges from 1 to 20 inclusive, or —COONR'$_4$, wherein R' is a hydrogen, or an alkyl group whose carbon number ranges from 1 to 4 inclusive.

10 Claims, 7 Drawing Sheets

PYRIDINE DERIVATIVE AND ITS COMPLEX

BACKGROUND OF THE INVENTION

1. Field of the Invention

The present invention relates to a pyridine derivative and its ruthenium or osmium complex.

2. Discussion of the Background

A dye sensitizing type solar battery which employs a compound having photoelectric exchanging function is described in U.S. Pat. No. 5,463,057. Bipyridine and a ruthenium complex of tetrabipyridine are disclosed as examples for compounds having photoelectric exchanging function.

SUMMARY OF THE INVENTION

It is an object of the present invention to provide a novel pyridine derivative and its complex.

This and other objects have been achieved according to the present invention, the first embodiment of which includes a pyridine compound represented by the following formula (I)

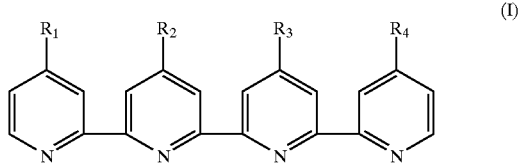

wherein each of $R_1$, $R_2$, $R_3$, $R_4$ is independently —OR', —COOR', —CONR', —CHO, —CH$_2$OR', —CN, an alkyl group whose carbon number ranges from 1 to 20 inclusive, or —COONR'$_4$, wherein R' is a hydrogen, or an alkyl group whose carbon number ranges from 1 to 4 inclusive.

Another embodiment of the present invention includes a complex of a pyridine compound represented by the following formula (II)

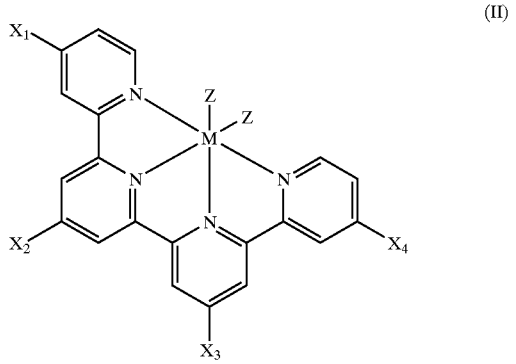

wherein each of $X_1$, $X_2$, $X_3$, $X_4$ is independently —OR, —COOR', —CONR', —CHO, —CH$_2$OR', —CN, an alkyl group whose carbon number ranges from 1 to 20-inclusive, or —COONR'$_4$, wherein R' is a hydrogen, or an alkyl group whose carbon number ranges from 1 to 4 inclusive;

wherein Z is Cl, Br, CN, NCS, or NCO; and wherein M is Ru or Os.

BRIEF DESCRIPTION OF THE DRAWINGS

The above and other objects, features and advantages of the present invention will be more apparent and more readily appreciated from the following detailed description of preferred exemplary embodiments of the present invention, taken in connection with the accompanying drawings, in which.

DETAILED DESCRIPTION OF THE PRESENT INVENTION

Figure 1:
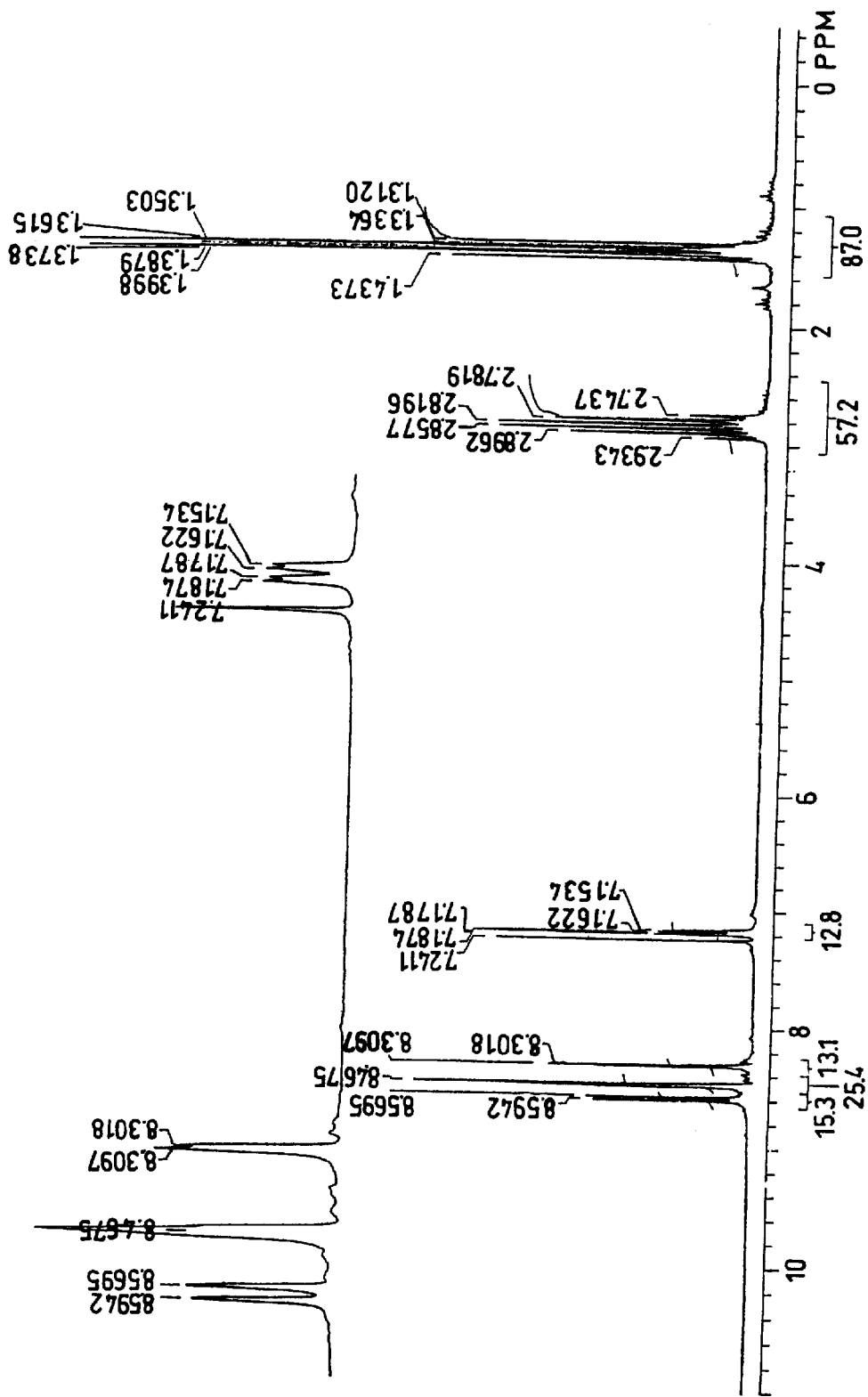
FIG. 1 is an NMR spectrum of a pyridine derivative according to Example 1.

A complex represented by the following formula (II) and produced from a pyridine derivative tetramer represented by the following formula (I) is superior in absorption peak shift to higher wavelengths which results in effective solar light absorption, when compared to the compounds disclosed in the foregoing U.S. Pat. No. 5,463,057.

It is to be noted that the existence of the pyridine derivative according to the present invention was not found or suggested due to very, very small yield thereof in the conventional pyridine polymer synthesis. The present inventors were confident of the higher performance of a pyridine tetramer derivative. Thus, they conducted research by employing reaction conditions including a large amount of raw material and longer reaction time. This research resulted in the synthesis of a pyridine tetramer derivative.

Preferably, the pyridine derivative in accordance with the present invention is a compound which is represented by the following formula (I)

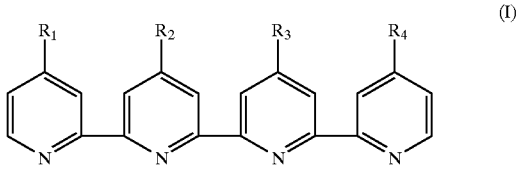

in which each of $R_1$, $R_2$, $R_3$, $R_4$ is independently selected from —OR', —COOR', —CONR', —CHO, —CH$_2$OR', —CN, an alkyl group whose carbon number ranges from 1 to 20 inclusive, or —COONR'$_4$, where R' is a hydrogen or an alkyl group whose carbon number ranges from 1 to 4 inclusive.

In addition, the complex of the pyridine derivative of the present invention is a compound which is represented by the following formula (II)

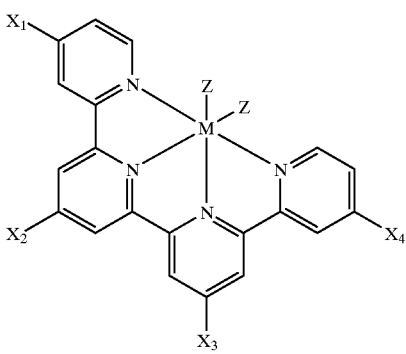

(II)

in which each of $X_1$, $X_2$, $X_3$, $X_4$ is independently selected from —OR', —COOR', —CONR', —CHO, —CH$_2$OR, —CN, an alkyl group whose carbon number ranges from 1 to 20 inclusive, or —COONR'$_4$, where R' is a hydrogen or an alkyl group whose carbon number ranges from 1 to 4 inclusive, Z is Cl, Br, CN, NCS, or NCO, and M is Ru or Os.

In formula (I), the alkyl group to be selected for each of $R_1$, $R_2$, $R_3$, $R_4$, is preferably methyl, ethyl, n-propyl, isopropyl, n-butyl, isobutyl, t-butyl and n-pentyl. Particularly preferable are ethyl and isopropyl.

The alkyl group whose carbon number ranges from 1 to 4 and which is represented by R', is preferably methyl, ethyl, n-propyl, isopropyl, n-butyl, isobutyl and t-butyl.

The pyridine derivative which is represented by formula (I) is preferably a compound in which all $R_1$, $R_2$, $R_3$, $R_4$ are an ethyl group or an isopropyl group or a compound in which all $R_1$, $R_2$, $R_3$, $R_4$ are a carboxyl group or its ester.

Particularly preferable are 4,4',4",4'"-tetraethyl-[2,2';6', 2"6",2"'] quaterpyridine, 4,4',4",4'"-tetraisopropyl [2,2';6', 2";6",2"']quaterpyridine, [2,2';6',2";6",2"']quaterpyridine-4, 4',4",4'"-tetracarboxylic acid, and [2,2';6',2";6",2"'] quaterpyridine-4,4',4",4'"-tetracarboxylic acid tetra ester.

The complex of the pyridine derivative which is represented by formula (I) is preferably a compound in which $X_1$ and $X_4$ are the same, $X_2$ and $X_3$ are the same, all $X_1$, $X_2$, $X_3$, $X_4$ are a carboxyl group, its ester, or its amide. Preferable Z and M are NCS and ruthenium, respectively.

Particularly preferable are, Ru(2,2',;6',2"6',2'"-quaterpyridine-4,4',4',4'"-tetracarboxylic acid tetra methyl ester)(NCS)$_2$, ((C$_2$H$_5$)$_3$NH)$_4$[Ru(2,2';6',2";6",2"'-quaterpyridine-4,4',4",4'"-tetracarboxylate)(NCS)$_2$], ((C$_4$H$_9$)$_3$N)$_n$H$_{4-n}$[Ru(2,2';6',2";6",2"'-quaterpyridine-4,4', 4",4'"-tetracarboxylate)(NCS)$_2$], and Ru(2,2';6',2";6",2"-quaterpyridine-4,4',4",4'"-tetracarboxylic acid)(NCS)$_2$.

The compounds in accordance with the present invention can be produced by conventional methods.

The pyridine derivative of the present invention can be obtained or produced by polymerizing the corresponding pyridine monomer or pyridine dimer. A synthetic method starting from a monomer is disclosed in, for example, U.S. Pat. No. 6,463,057 granted to Graetzel et al, J. Am. Chem. Soc., 99, 4047 (1977), and Inorg. Chem., 24, 4573 (1985). However, in this case the yield of the pyridine derivative is poor or very small. In each of these synthesis methods, a large amount of pyridine dimer/trimer derivative is produced as a by-product in addition to the pyridine tetramer derivative. In order to isolate the pyridine tetramer derivative from the mixture of these substances or compounds, well known methods such as distillation or column chromatography have to be used.

The pyridine derivative of formula (I) is a chelation agent or a (raw material) conductive polymer as well as an intermediate raw material for producing the complex of the pyridine derivative of formula (II).

The complex of the pyridine derivative of formula (II) has a very high in photoelectric exchanging function or activity and therefore can be used preferably as a coloring material for a dye sensitizing type solar battery. For example, a dye sensitizing type solar battery is made of a transparent substrate with a transparent conductive membrane, a conductive substrate opposed to the transparent substrate, and set of sensitizing dye carrying semiconductor electrodes and a catalytic layer which is interposed between the transparent substrate and the conductive substrate. In this solar battery, an electric energy is generated by a photoelectric exchanging function between the transparent membrane and the conductive substrate. The sensitizing dye is preferably the complex of the pyridine derivative of formula (II). A dye sensitizing type solar battery can be produced by forming an aluminum-doped oxidized titan layer as a semiconductor layer on a conductive substrate. An electrode in the form of a layer of a pyridine derivative complex according to the present invention is provided as a dye sensitizer on an outer surface of the oxidized titan layer. A transparent electrode which is formed of e.g. a conductive glass, and an electrolyte solution which includes, for example, iodine is filled between the electrodes. In the complex of the pyridine derivative of the present invention, electrons are found to be localized when compared to a dimer or trimer of a pyridine derivative. This shifts the maximum peak absorption wavelength toward a longer wavelength, a sunlight spectrum (energy) can be converted effectively into electric power.

The complex of the pyridine derivative of the present invention can be used as a coloring material similar to the conventional or existing coloring materials.

Having generally described this invention, a further understanding can be obtained by reference to certain specific examples which are provided herein for purposes of illustration only, and are not intended to be limiting unless otherwise specified.

EXAMPLES

Synthesis Example 1

Synthesis of 4,4',4",4"-tetraethyl-(2,2';6',2";6",2'")] quaterpyridine

In a flask, 500 ml of 4-ethyl pyridine which is commercially available and 20 g palladium carbon having a palladium content of 5% by weight were mixed. After a four-day reflux while the resulting mixture was stirred, the resulting mixture was filtered to eliminate palladium carbon. The resulting reaction product was distilled under reduced pressure to obtain the above identified quaterpyridine. In this example, 4,4'-diethyl-[2,2']bypyridine and 4,4',4"-triethyl-[2,2';6',2"]terpyridine were simultaneously produced and separated by the above distillation under reduced pressure.

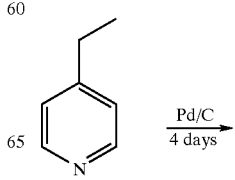

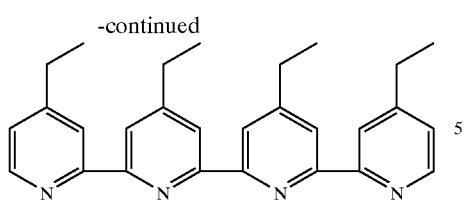

Synthesis Example 2

Synthesis of [2,2';6',2";6",2'"]quaterpyridine-4,4',4", 4'"-tetracarboxylic acid In a flask, 3.00 g (7.10 mmol) of the compound of Example 1, 90 ml of sulfuric acid were added and the resulting mixture was stirred until the compound of Example 1 was completely dissolved.

To the resulting liquid or solution, 16.70 g (56.80 mmol) of 2-potassium chromate were added so that the temperature increased from 30 to 60° C. over the course of six hours.

After an overnight reaction, 3 l of the resulting reaction solution were added to an amount of ice water and the resulting mixture was left standing overnight at a temperature of 5° C. to separate crystals from the mixture. Thereafter, the crystals were filtrated from the reaction solution. The resulting crystals were well washed with water and were dried in vacuum. The resulting crude-product and 10 ml of 50% nitric acid were placed in a flask and heated to 60° C. and the resulting mixture was stirred for 5 hours. After stirring, the resulting reaction solution was added to 2 l of ice water and left standing overnight at a temperature of 5° C. to separate crystals from of the mixture. Thereafter, the crystals were filtrated from the reaction solution. The resulting crystals were well washed with water and were dried in vacuum to obtain a white crystalline compound.

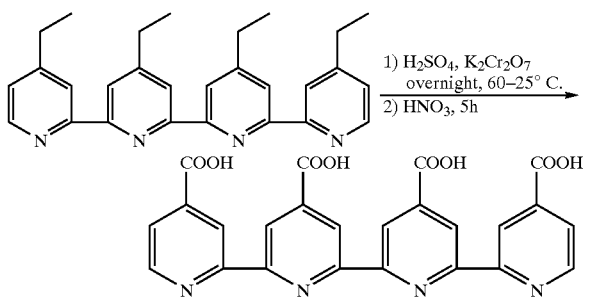

Synthesis Example 3-1

Synthesis of [2,2';6',2";6"2'"]quaterpyridine-4,4',4", 4'"-tetracarboxylic acid tetra methyl ester 3.30 g (6.79 mmol) of the compound of Example 2 were added to a flask and were refluxed under argon together with 300 ml of dried methanol and 6 ml of sulfuric acid and stirring for 2 days. After lowering the temperature of the solution to room temperature, the reaction solution was added to a solution of saturated sodium hydrogen carbonate. After ethanol elimination from the reaction solution under reduced pressure, a crystal was extracted from the reaction solution by filtering. The resulting crystal was well washed with water and was dried under vacuum to obtain a white crystalline compound.

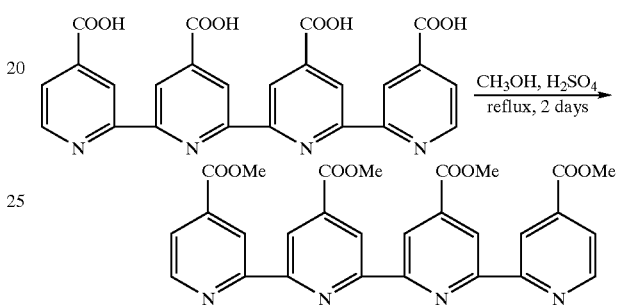

Synthesis Example 3-2

Synthesis of Ru(2,2';6',2";6',2'"-quaterpyridine-4,4', 4'"-tetracarboxylic acid tetra methyl ester)(NCS)$_2$ In a flask, 200 ml of DMF (dimethylformamide) and 174 mg of RuCl$_3$.nH$_2$O were added under argon and the resulting mixture was stirred for 1.5-hours at a temperature of 80° C. and then added to 500 mg (0.922 mmol) of the compound of Example 3-1 to react for 5 hours at a temperature of 160° C. Thereafter, the reaction solution was added to 1.913 g (25.1 mmol)/2 ml of ammonium thiocyanate solution and the resulting mixture was stirred overnight at a temperature of 140° C. The reaction solution was cooled down to room temperature, its solvent amount was reduced to about 10 ml, about 100 ml of water were added, and the mixture was left standing overnight at a temperature of 5° C. to separate a crystal. The crystal was extracted by filtering, washed with water, and was dried under vacuum to obtain a white crystalline material.

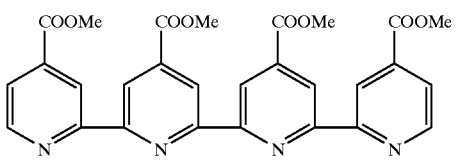

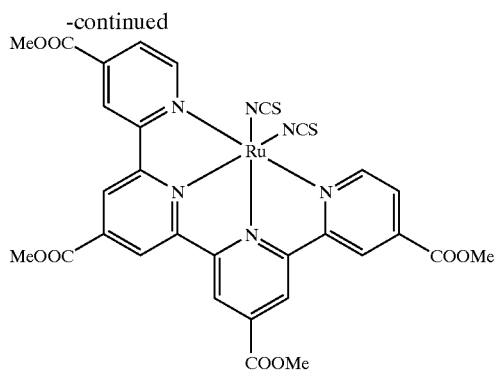

Synthesis Example 3-3

Synthesis of $((C_2H_5)_3NH)_4[Ru(2,2';6,2'';6',2'''-$quaterpyridine-4,4',4'',4'''-tetracarboxylate)$(NCS)_2]$ In a flask, 700 mg (0.921 mmol) of the compound of Example 3-2 were added under argon to 53 ml of DMF, 701 mg (9.21 mmol)/21 ml of ammonium thiocyanate solution, and 6 ml of triethylamine. The resulting mixture was stirred for 2 days at a temperature of 30° C. After the reaction solution was cooled down to room temperature, its solvent amount was reduced under reduced pressure to about 10 ml. About 100 ml of water were added, and the mixture was left standing overnight at a temperature of 5° C. to separate a crystal. The crystal was extracted by filtering, washed with water, and dried under pressure reduction. The resulting crude product was added to a flask under argon, 53 ml of DMF, 701 mg (9.21 mmol)/21 ml of ammonium thiocyanate solution, and 6 ml of triethylamine were added. The resulting mixture was stirred for 2 days at a temperature of 110° C. After the reaction solution was cooled down to room temperature, its solvent amount was reduced under reduced pressure to about 10 ml. About 100 ml of water were added, and the mixture was left to stand overnight at a temperature of 5° C. to separate a crystal. The crystal was extracted by filtering, washed with water, and dried under vacuum to obtain a black crystal.

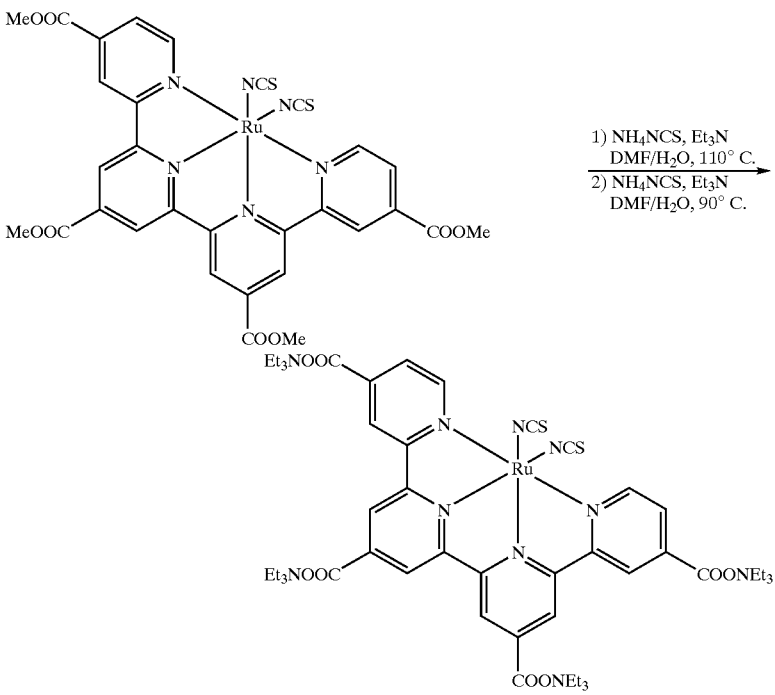

Synthesis Example 3-4

Synthesis of $((C_4H_9)_3N)nH4-n[Ru(2,2';6',2'';6'',2'''-$quaterpyridine-4,4',4'',4'''-tetracarboxylate)$(NCS)_2]$ 2.0 g of the compound of Example 3-3, 2.4 g of tetra-n-butyl-ammonium-thiocyanate, and 30 ml of water were added to a beaker and stirred. The resulting mixture was added, until its pH became 9–10, to a 10% solution of tetra-n-butyl-ammonium-hydroxide. After dissolving of the deposit resulting from stirring the liquid at pH 9–10, the solution was filtered to remove impurities. Thereafter, the pH of the solution was adjusted to 4.80 with nitric acids having concentrations of 1N, 0.1N, and 0.01N. The resulting solution was left to stand overnight at a temperature of 5° C.

to separate a crystal. The crystal was extracted by filtering and was dried under reduced pressure. The resulting crude product was refined using a gel column. The resulting solution was reduced under pressure reduction, condensed to 10 ml and thereafter, until its pH became 9–10, a 10% solution of tetra-n-butyl-ammonium-hydroxide was added. After dissolving of the deposit resulting from stirring the liquid at pH 9–10, the solution was filtered to remove impurities. Thereafter, the pH of the solution was again adjusted to between 5.20 and 1.50 with nitric acids to obtain compounds which are different in 'n' (n: 0–4).

added. The resulting mixture was, after being added to 500 ml of DMF, stirred for four hours at a temperature of 140° C. under argon. The mixture was cooled down to 120° C. and was stirred, after addition of 3.1 g (41 mmol)/100 ml of ammonium thiocyanate solution for 2 hours. Then, after cooling the reaction solution down to room temperature, the separated crystal was extracted by filtering, washed with water and dried under vacuum. 2 g of the resulting crude product, 2.4 g of tetra-n-butyl-ammonium-thiocyanate, and 30 ml of water were added into a beaker to stir. The resulting

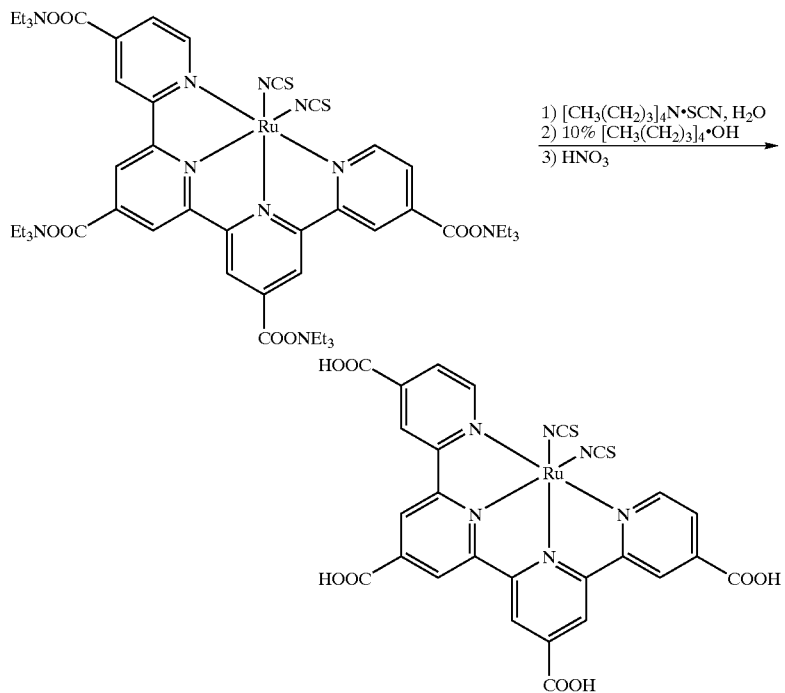

Synthesis Example 4-1

Synthesis of [RuCl$_2$(DMSO)$_4$]

10 ml of dimethyl sulfoxide were added to a flask and warmed up to a temperature of 80° C. Then, the dimethyl sulfoxide was, after being combined with 4 g of [RuCl$_3$.nH$_2$O], stirred for a time duration of ten minutes. The resulting solution was cooled down to room temperature, added to 50 ml of acetone, and left to stand for an hour at a temperature of 5° C. to separate a crystal. The crystal was extracted by filtering and dried, under vacuum, to obtain a copper-colored crystal.

Synthesis Example 4-2

Synthesis of [Ru(2,2';6',2";6";2'''-quaterpyridine-4,4',4",4'''-tetracarboxylate)(NCS)$_2$]

To a flask, 2 g of the compound of Example 4-1 and 2 g (4.1 mmol) of the compound made in Example 2 were mixture was added, until its pH became 9–10, to a 10% solution of tetra-n-butyl-ammonium-hydroxide. After dissolving of the deposit resulting from stirring the liquid at pH 9–10, the solution was filtered to remove impurities. Thereafter, the pH of the solution was adjusted to 4.80 with nitric acids having concentrations of 1N, 0.1N, and 0.01N. The resulting solution was left standing overnight at a temperature of 5° C. to separate a crystal. The crystal was extracted by filtering and was dried under reduced pressure.

The resulting crude product was melted and refined with a gel column. The resulting solution was, under pressure reduction, condensed to about 10 ml and added, until its pH became 9–10, to a 10% solution of tetra-n-butyl ammonium-hydroxide. After dissolving of the deposit resulting from stirring the liquid pH 9–10, the solution was filtered to remove impurities. Thereafter, the pH of the solution was again adjusted to between 5.20 and 1.50 with nitric acids to obtain a black crystal.

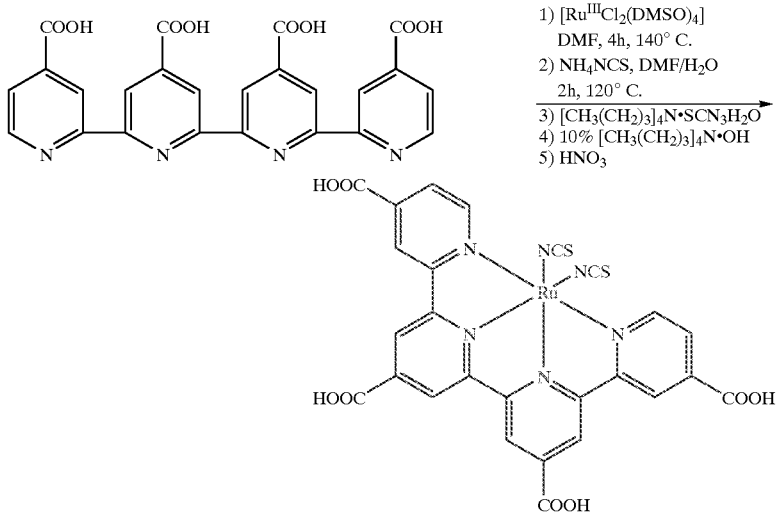

Synthesis Example 5

The ruthenium complex of each of 4,4'-diethyl-[2,2'] bipyridine and, 4,4',4"-triethyl-[2,2';6',2"]terpyridine is synthesized in a similar fashion as described in each of Examples 2 to 4. The ruthenium complex synthesized from the 4,4'-diethyl-[2,2'] bipyridine is a red crystal, while the ruthenium complex synthesized from the 4,4',4"-triethyl-[2,2';6',2"]terpyridine is a green crystal.

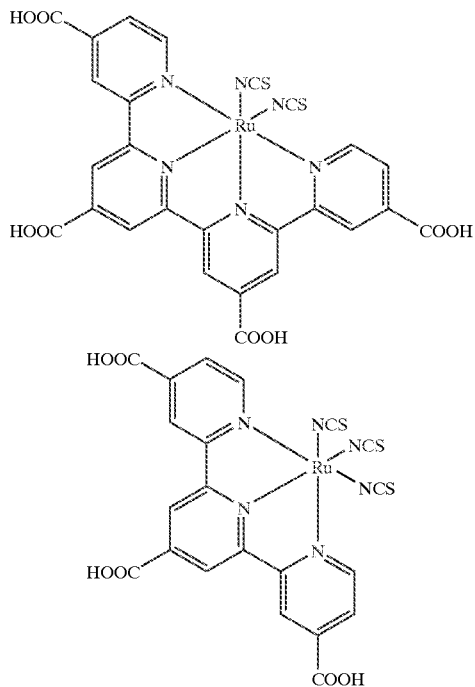

Product Identification

The structure of each of the above substances was identified by way of nuclear magnetic resonance analysis (NMR), ultraviolet visual ray spectroscopy (UV-VIS), high-speed liquid chromatography, mass spectrometry, and elemental analysis.

Figure 2:
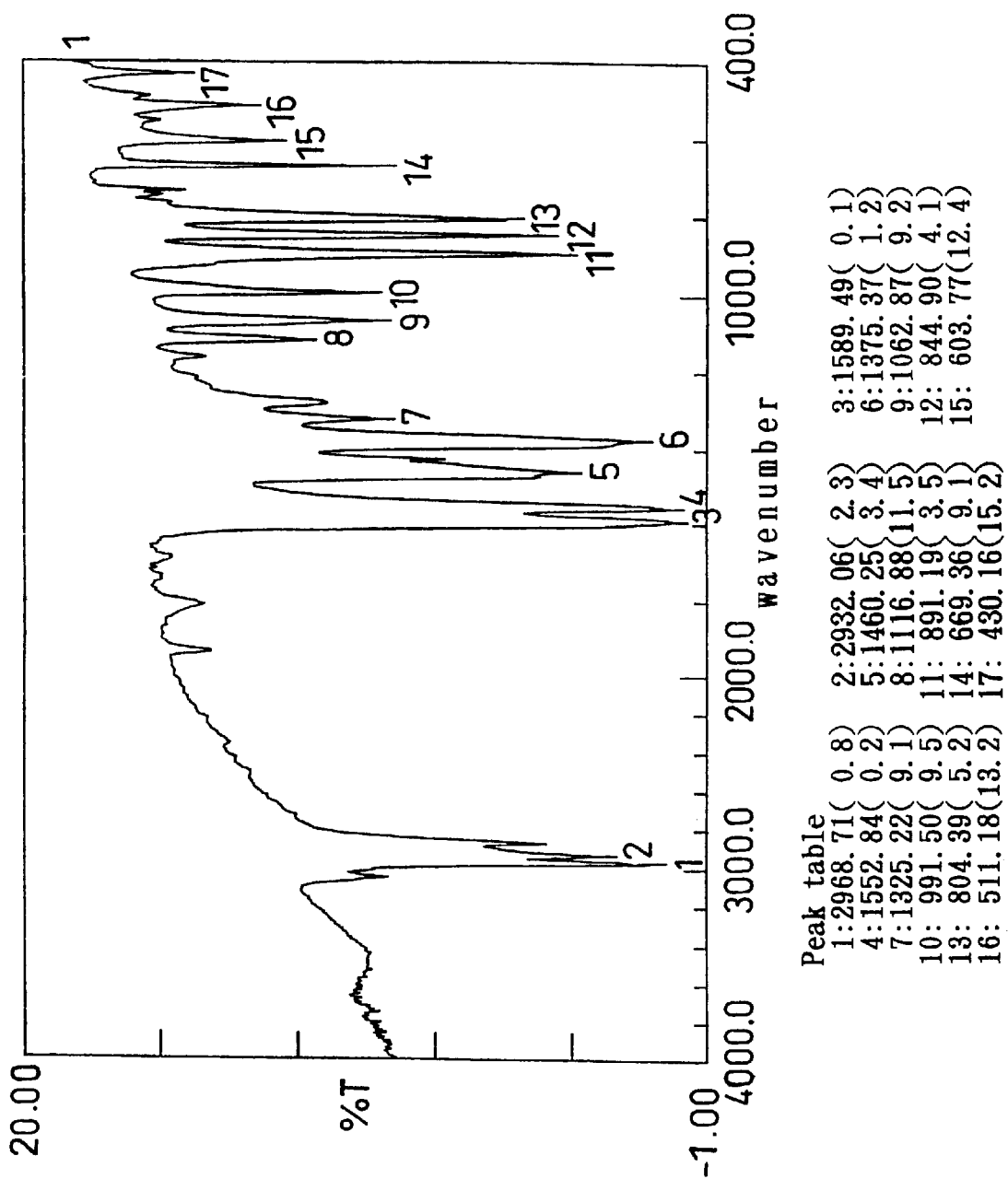
FIG. 2 is an IR spectrum of the pyridine derivative according to Example 1.

(1) With respect to the Example 1, its NMR spectrum and IR spectrum are illustrated in FIG. 1 and FIG. 2, respectively. As apparent from FIG. 1, the peak of chemical shift δ 8.58 ppm (2H,d,J=4.9) corresponds to 6-position of hydrogen and 6'''-position of hydrogen, the peak of chemical shift δ 8.46 ppm (4H,s) corresponds to 5'-position of hydrogen, 3"-position of hydrogen, 3'-position of hydrogen, and 5"-position of hydrogen, the peak of chemical shift δ 8.31 ppm (2H,d,j=1–6) corresponds to 3-position of hydrogen and 3'''-position of hydrogen, and the peak of chemical shift δ 7.17 ppm (2H,d,J=5.0;1,7) corresponds to 5-position of hydrogen and 5'''-position of hydrogen.

And as apparent from FIG. 2, the peak of 3050 cm$^{-1}$(w) and the peak of 3000–2800 cm$^{-1}$(m) correspond to the pyridine and —$CH_2CH_3$. Thus, the present compound can be characterized by NMR spectrum and IR spectrum.

In addition, the present compound can be characterized by mass spectrometry and elemental analysis.

Figure 3:
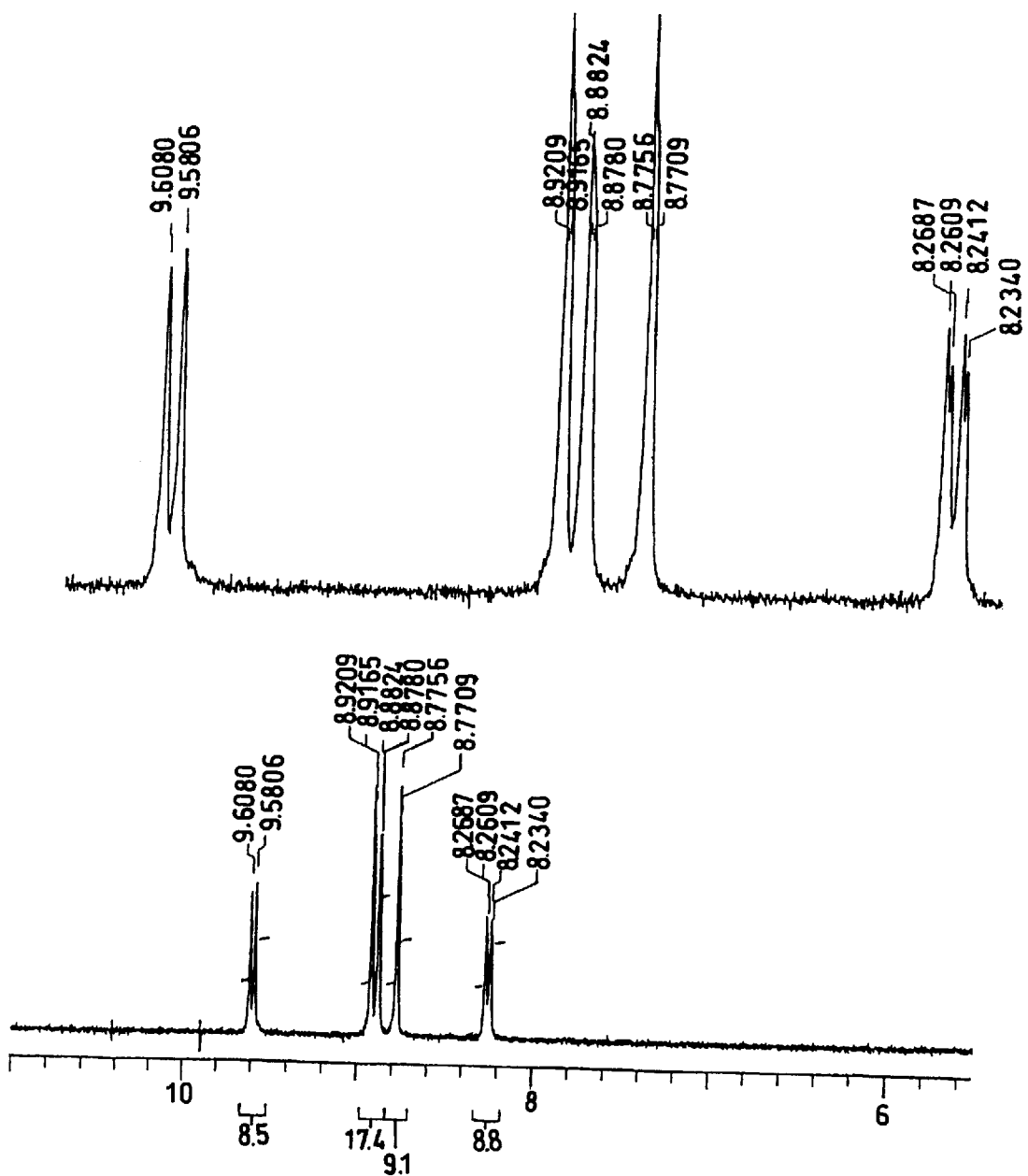
FIG. 3 is an NMR spectrum of a complex of a pyridine derivative according to synthetic Examples 3 and 4.
Figure 4:
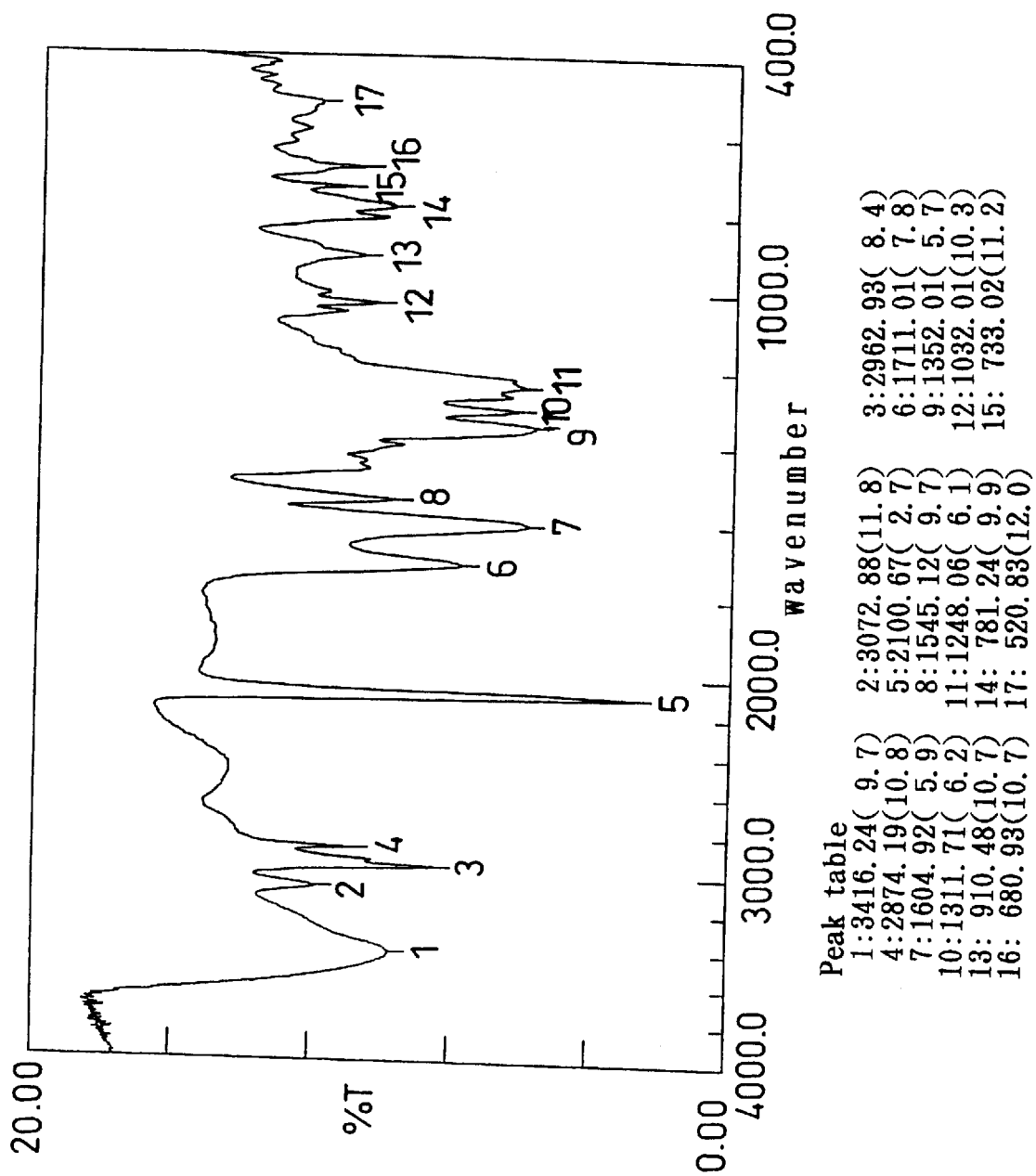
FIG. 4 is an IR spectrum of the complex of pyridine derivative according to Examples 3 and 4.

(2) With respect the Example 2, its NMR spectrum and IR spectrum are illustrated in FIG. 3 and FIG. 4, respectively.

As apparent from FIG. 3, the peak of chemical shift δ 9.57 ppm (2H,d,J=,5.5) corresponds to 6-position of hydrogen and 6'''-position of hydrogen, the peak of chemical shift δ' 8.92 ppm (2H, d,J=0.9) corresponds to 5'-position of hydrogen and 3"-position of hydrogen, the peak of chemical shift δ 8.88 ppm (2H,d,J –0.9) corresponds to the 3'-position of hydrogen and 5"-position of hydrogen, the peak of chemical shift δ 8.77 ppm (2H,d,J=0.9) corresponds to the 3-position of hydrogen and the 3'''-position of hydrogen, and the peak of shift δ 8.25 ppm (2H,dd,J=5.5; 1.6) corresponds to the 5-position of hydrogen and 5'''-position of hydrogen.

And as apparent from FIG. 4, the peak of 3600–2500 cm$^{-1}$(b), the peak of 3073 cm$^{-1}$(w), the peak of 3000–2900 cm$^{-1}$(m), the peak of 2101 cm$^{-1}$(s), the peak of 1,711 cm$^{-1}$(m), and the peak of 1605 cm$^{-1}$(m) corresponds to OH, pyridine skeleton, TBA, NCS, CO, and CO, respectively. Thus, the present compound can be characterized by NMR spectrum and IR spectrum.

In addition, the compound of Example 2 can be characterized by mass spectrometry and elemental analysis.

Figure 5:
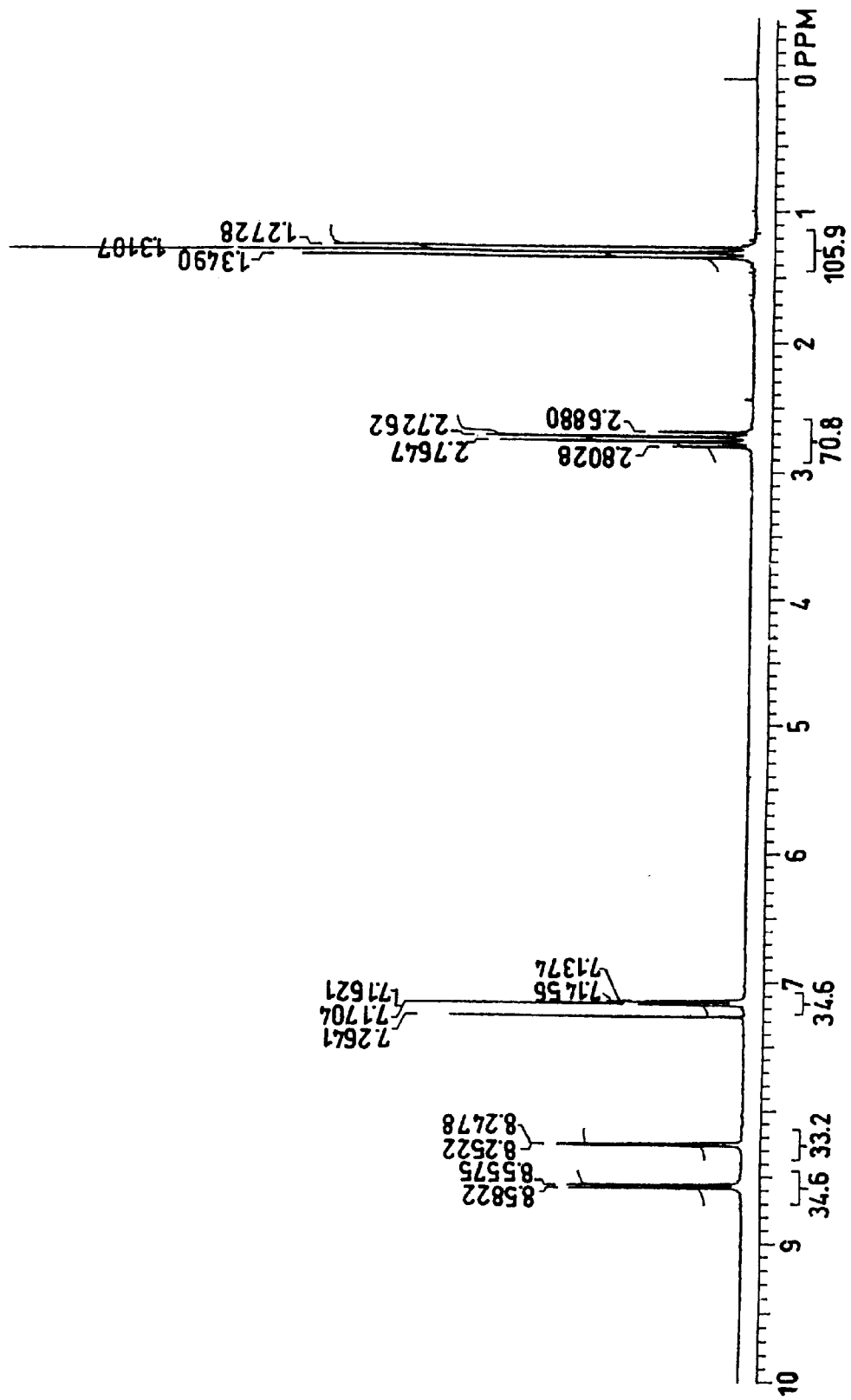
FIG. 5 is an NMR spectrum of a pyridine dimer according to Example 5.
Figure 6:
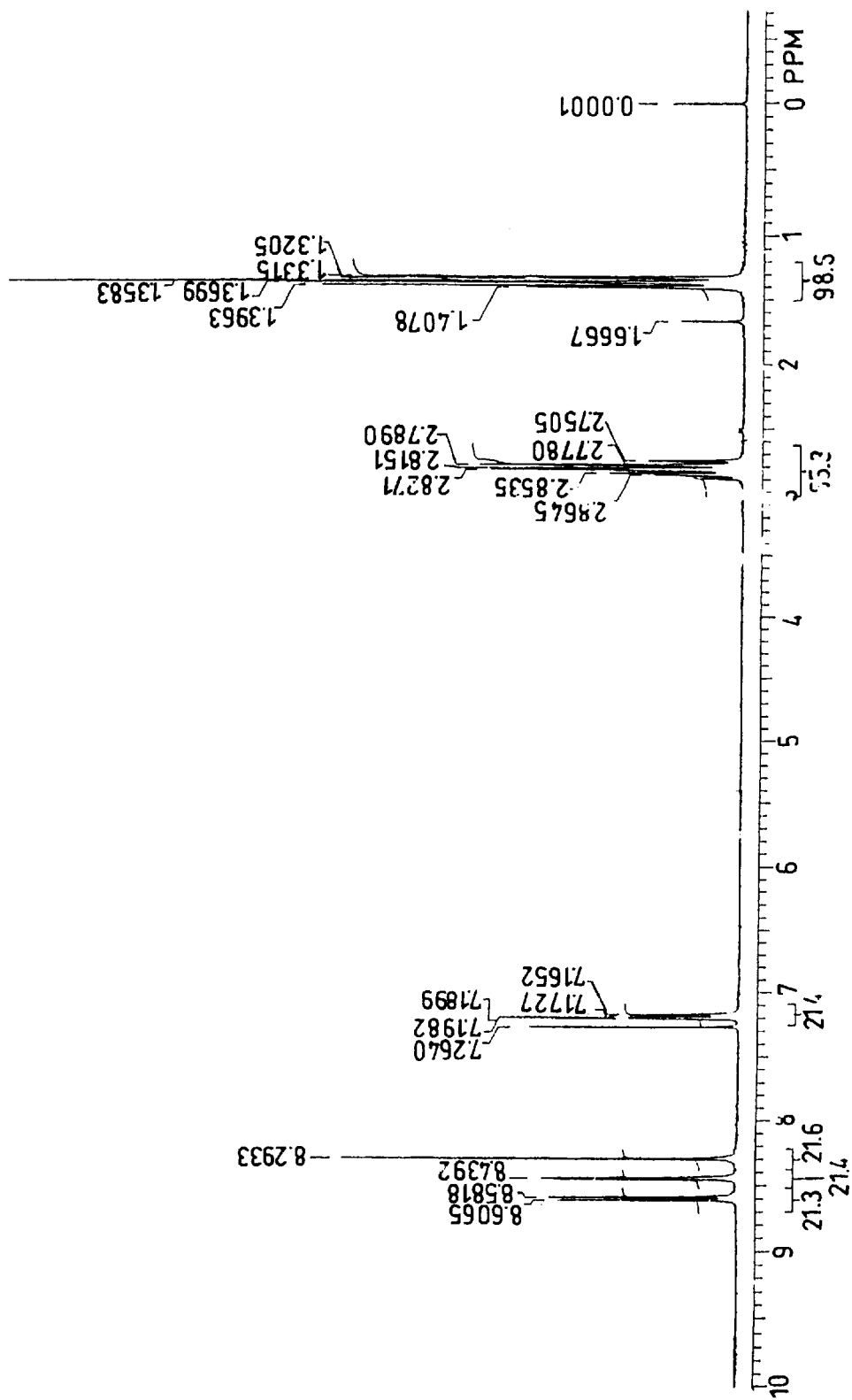
FIG. 6 is an NMR spectrum of a pyridine dimer according to Example 6.

For convenience, FIG. 5 and FIG. 6 illustrate NMR spectrums of the respective derivatives of 4, 4'-diethyl-[2,2'] bipyridine and of 4,4',4"-triethyl-[2,2';6',2"]terpyridine.

Figure 7:
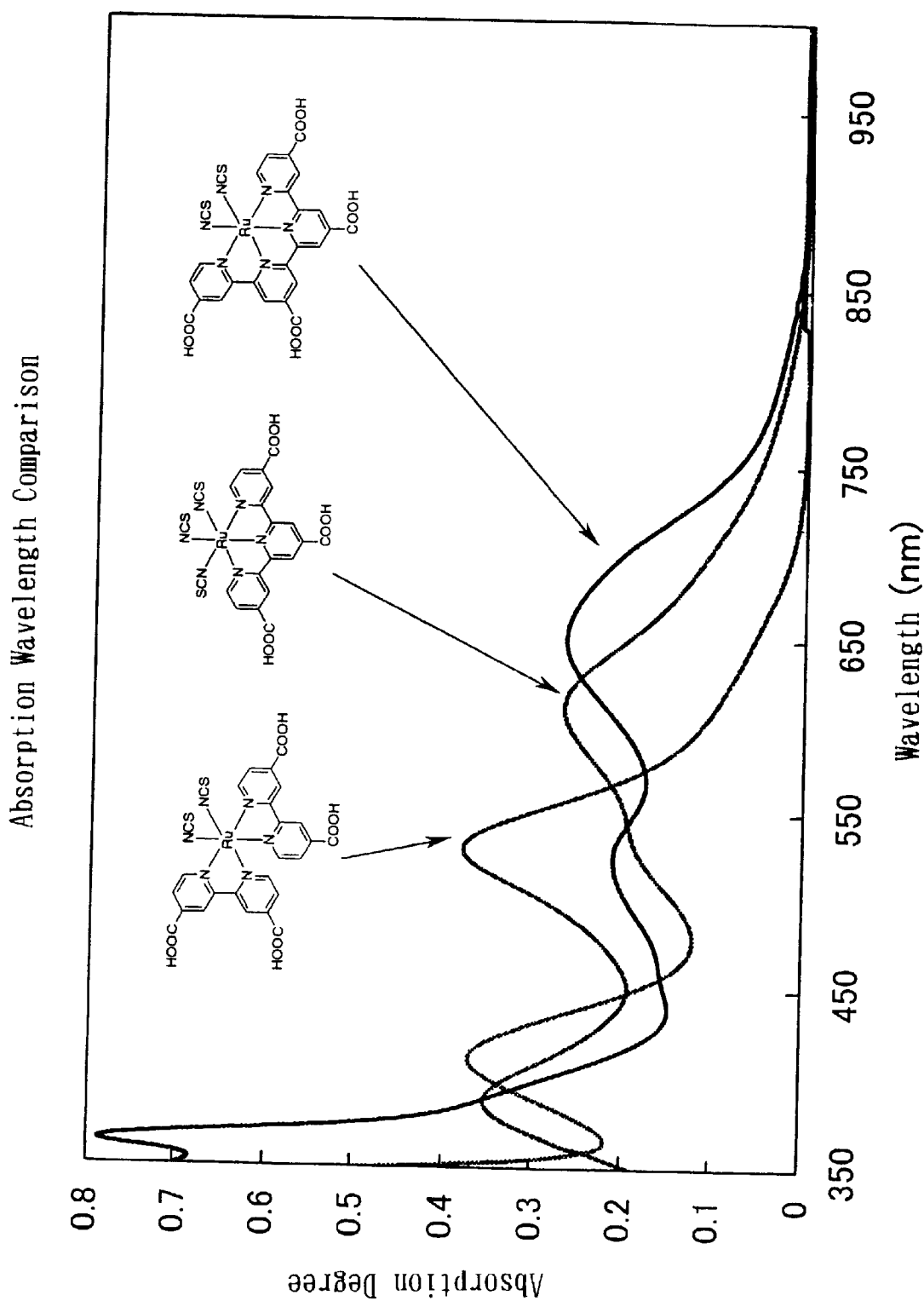
FIG. 7 is a UV-VIS absorption spectrum of a complex of a pyridine derivative.

UV-VIS absorption spectroscopy of each complex of pyridine derivative: photoelectric transfer characteristic FIG. 7 shows the complex of ruthenium which is synthesized from each of the carbonic acid derivatives of pyridine dimer, pyridine trimer, and pyridine tetramer. The measurement of absorption spectrum was performed such that each compound was dissolved in ethanol. The colors of the respective pyridine dimer, pyridine trimer, and pyridine tetramer are red, green, and blue violet. As apparent from FIG. 7, whenever the polymerization degree of pyridine increases, its absorption wavelength shifts to a longer wavelength. Thus, a large overlap between the solar light spectrum and the spectrum of the compound (complex of pyridine tetramer derivative) in accordance with the present invention occurs. This proves that the complex of the pyridine tetramer derivative may be used as dye sensitizing element which makes it possible to increase photoelectric exchanging performance when compared to a complex of pyridine dimer or trimer derivative as dye sensitizing element.

Japanese Patent Application No. 2000-389181, filed Dec. 21, 2000 (12th Year of Heisei) is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A pyridine compound represented by the following formula (I)

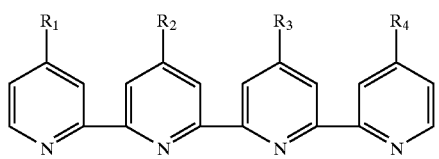

(I)

wherein each of $R_1$, $R_2$, $R_3$, $R_4$ is independently —OR', —COOR', —CONR', —CHO, —CH$_2$OR', —CN, an alkyl group whose carbon number ranges from 1 to 20 inclusive, or —COONR'$_4$, wherein R' is a hydrogen, or an alkyl group whose carbon number ranges from 1 to 4 inclusive.

2. The pyridine compound according to claim 1, wherein each of $R_1$, $R_2$, $R_3$, $R_4$ is an ethyl group or an isopropyl group.

3. The pyridine compound according to claim 1, wherein each of $R_1$, $R_2$, $R_3$, $R_4$ is a carboxyl group or a carboxyl ester.

4. A complex of a pyridine compound represented by the following formula (II)

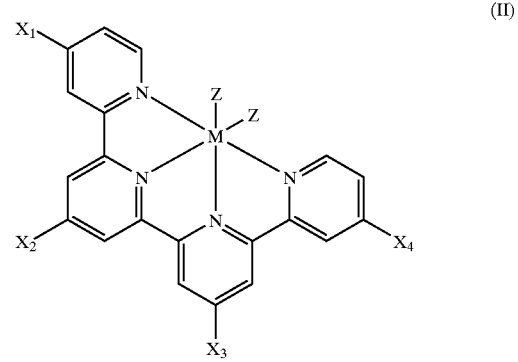

(II)

wherein each of $X_1$, $X_2$, $X_3$, $X_4$ is independently —OR, —COOR', —CONR', —CHO, —CH$_2$OR', —CN, an alkyl group whose carbon number ranges from 1 to 20-inclusive, or —COONR'$_4$, wherein R' is a hydrogen, or an alkyl group whose carbon number ranges from 1 to 4 inclusive;

wherein Z is Cl, Br, CN, NCS, or NCO; and wherein M is Ru or Os.

5. The complex of the pyridine compound according to claim 4, wherein $X_1$ and $X_4$ are the same and $X_2$ and $X_3$ are the same, respectively.

6. The complex according to claim 4, wherein Z is NCS and M is Ru.

7. The complex according to claim 4, wherein each of $X_1$, $X_2$, $X_3$, $X_4$ is independently a carboxyl group or an amid group.

8. The pyridine compound according to claim 1, which is 4,4',4'',4'''-tetraethyl-[2,2';6',2''6'',2''']quaterpyridine, 4,4',4'', 4'''-tetraisopropyl [2,2';6'2'';6''2''']quaterpyridine, [2,2';6', 2'';6'',2''']quaterpyridine-4,4',4'',4'''-tetracarboxylic acid, or [2,2';6',2'';6'',2''']quaterpyridine-4,4',4'',4'''-tetracarboxylic acid tetra ester.

9. The complex according to claim 4, wherein M is Os.

10. A dye sensitizing solar battery, comprising:

a transparent substrate;

a transparent conductive membrane;

a conductive substrate opposed to the transparent substrate;

a set of sensitizing dye carrying semiconductor electrodes; and a catalytic layer;

wherein said sensitizing dye is the complex according to claim 4.

* * * * *